(12) United States Patent
Reichert et al.

(10) Patent No.: US 8,642,790 B2
(45) Date of Patent: Feb. 4, 2014

(54) PROCESS FOR PREPARING 5-HYDROXYMETHYLFURFURAL VIA 5-ACYLOXYMETHYLFURFURAL AS AN INTERMEDIATE

(75) Inventors: Dietmar Reichert, Eschau (DE); Martin Sarich, Alzenau (DE); Friedhelm Merz, Nierstein (DE)

(73) Assignee: Evonik Degussa GmbH, Essen (DE)

( * ) Notice: Subject to any disclaimer, the term of this patent is extended or adjusted under 35 U.S.C. 154(b) by 1628 days.

(21) Appl. No.: 12/031,983

(22) Filed: Feb. 15, 2008

(65) Prior Publication Data

US 2008/0200698 A1    Aug. 21, 2008

(30) Foreign Application Priority Data

Feb. 16, 2007 (DE) .......................... 10 2007 007 629

(51) Int. Cl.
*C07D 307/34* (2006.01)
*C07D 307/48* (2006.01)
*C07D 307/50* (2006.01)

(52) U.S. Cl.
USPC ........................................ 549/488; 549/489

(58) Field of Classification Search
USPC ................................. 549/488, 489
See application file for complete search history.

(56) References Cited

FOREIGN PATENT DOCUMENTS

| DE | 33 09 564 A1 | 9/1984 |
| EP | 1 834 951 A1 | 9/2007 |
| GB | 925812 | 5/1963 |

OTHER PUBLICATIONS

Jaroslaw Lewkowski. Synthesis, chemistry and applications of 5-hydroxymethylfurfural and its derivatives. http://www.arkat-usa.org/get-file/20028/. ARKIVOC (i) (2001) 17-54.*
Bicker, M. Dehydration of D-fructose to hydroxymethylfurfural in sub- and supercritical fluids. J. of Supercritical Fluids. 36 (2005) 118-126.*
Nimlos et al. [Nimlos, Mark R. Enhancement of 1,2-dehydration of alcohols by alkali cations and protons: a model for dehydration of carbohydrates. J. Anal. Appl. Pyrolysis. 66 (2003) 3-27.*
Claude Moreau, et al. "Recent Catalytic Advances in the Chemistry of Substituted Furans from Carbohydrates and in the Ensuing Polymers" Chemistry of substituted furans, vol. 27, No. 1-4, (pp. 11-30), Feb. 2004.
Office Action issued Oct. 10, 2011 in Chinese Application No. 200810080742.4 (With English Translation).

* cited by examiner

*Primary Examiner* — Samantha Shterengarts
(74) *Attorney, Agent, or Firm* — Oblon, Spivak, McClelland, Maier & Neustadt, L.L.P.

(57) ABSTRACT

5-hydroxymethylfurfural of the formula II

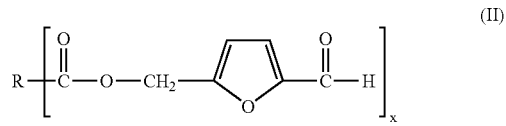

is prepared via a 5-acyloxymethylfurfural as an intermediate.

14 Claims, No Drawings

PROCESS FOR PREPARING 5-HYDROXYMETHYLFURFURAL VIA 5-ACYLOXYMETHYLFURFURAL AS AN INTERMEDIATE

BACKGROUND OF THE INVENTION

1. Field of the Invention

The present invention relates to a novel process for preparing 5-hydroxymethylfurfural via a 5-acyloxymethylfurfural as an intermediate. The invention also relates to a novel process for preparing the 5-acyloxymethylfurfural intermediate.

2. Discussion of the Background

5-Hydroxymethylfurfural of the following formula (I)

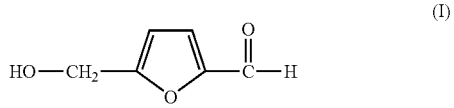

has, among other properties, antibacterial and corrosion-inhibiting properties and is suitable for a multitude of reactions. It is possible without any great difficulty to prepare furfuryl-dialcohol, -dialdehyde and -dicarboxylic acid and their derivatives therefrom; equally, the hydrogenation of the ring leads to difunctional 2,5-tetrahydrofuran derivatives. Difunctional furan derivatives substituted differently on C-2 and C-5 are also readily obtainable from 5-hydroxymethylfurfural. The aforementioned and other useful organic intermediates preparable from 5-hydroxymethylfurfural serve to prepare numerous chemical products, for instance solvents, surfactants, crop protectants and resins. In addition, the use of 5-hydroxymethylfurfural for treatment of malignant tumours has been reported (U.S. Pat. No. 5,006,551).

5-Hydroxymethylfurfural is an intramolecular, triple dehydration product of hexoses (aldohexoses and ketohexoses). Renewable raw materials, such as starch, cellulose, sucrose or inulin, are inexpensive starting substances for preparing hexoses, such as glucose and fructose. 5-Hydroxymethylfurfural is in principle an intermediate of the dehydrating decomposition of hexoses to laevulinic acid and formic acid, i.e. what is crucial is to stop the reaction at the correct time. This makes the removal of 5-hydroxymethylfurfural from the starting sugars and by-products an important step in its preparation.

A large number of different processes for preparing 5-hydroxymethylfurfural on the laboratory scale is already known.

The catalysts which have been described for the dehydration are different acids or salts, for example oxalic acid (cf. W. N. Haworth et al., J. Chem. Soc. 1944, 667), salts such as pyridine hydrochloride (cf. C. Fayet et al., Carbohydr. Res. 122, 59 (1983)), acidic ion exchangers (cf. DE-A-30 33 527) or Lewis acids such as zirconyl chloride (cf. SU-A-1 054 349, cit. CA 100, 120866s) or boron trifluoride etherate (cf. H. H. Szmant et al., J. Chem. Tech. Biotechnol 31, 135 (1981)).

For the industrial scale preparation of 5-hydroxymethyl-furfural the catalyst used should be inexpensive and non-corrosive. Solid catalysts intended for reuse are, owing to the easy manner of formation of insoluble by-products, unsuitable because a removal of the catalyst (e.g. ion exchanger) from these by-products is uneconomic or impossible.

Lewis acids such as zirconyl chloride or aluminium chloride likewise have to be rejected on the basis of considerations relating to corrosion protection. The use of sulphuric acid or phosphoric acid is therefore considered to be favourable, since the acidic aqueous reaction solutions can optionally be neutralized with bases in this case, and, for instance in the case of use of calcium hydroxide or calcium carbonate, the conversion of the catalyst acids to sparingly soluble salts with removal by filtration is possible.

The reaction medium of the dehydration of saccharides is determined by their solubility. In addition to water, dipolar aprotic solvents in particular, such as dimethylformamide or dimethyl sulphoxide, have been used.

The iodine-catalysed conversion of the fructose portion of sucrose to 5-hydroxymethylfurfural by heating sucrose in anhydrous dimethylformamide entails, as well as the expensive solvent, also a complicated workup, specifically extraction and paper chromatography (cf. T. G. Bonner et al., J. Chem. Soc. 1960, 787).

In the decomposition of fructose with different catalysts, good yields (>90%) of 5-hydroxymethylfurfural are found in dimethyl sulphoxide (cf. H. H. Szmant et al., J. Chem. Tech. Biotechnol. 31, 135 (1981)). However, the isolation of the desired product is difficult owing to the high boiling point of the solvent among other reasons, and entails a multistage extraction.

DE-A-33 09 564 therefore proposes, for the isolation of the 5-hydroxymethylfurfural from solutions comprising dimethyl sulphoxide, a derivatization to 5-acetoxymethylfurfural. As well as a vacuum distillation, this also entails two reaction steps (acetylization, deacetylization) and hence consumption of time and chemicals.

Several processes use mixtures of water and organic solvents as a reaction medium. In U.S. Pat. No. 2,929,823, furfural is added to aqueous saccharide solutions and heated briefly (0.1-120 s) to 250-380° C. Tar-like by-products are dissolved by the organic solvent added, as is 5-hydroxymethylfurfural. The preparation of 5-hydroxymethylfurfural in pure form thus appears to be performable only with difficulty.

A further biphasic process is described in DE-A-30 33 527. In this process, under relatively mild conditions (below 100° C.), fructose-containing aqueous solutions are decomposed with acidic cation exchangers, an organic solvent which is not water-miscible but nevertheless has a good distillation capacity for 5-hydroxymethylfurfural being present. The great disadvantage of this process is that a very large excess of the organic solvent, based on the aqueous phase (>7:1), is needed, and the solvents required are expensive and toxic. Moreover, the very good solubility of 5-hydroxymethylfurfural in water makes any extraction of the product with organic solvents from aqueous solutions exceptionally difficult.

The publication by C. Fayet et al., Carbohydr. Res. 122 (1983), 59, describes the decomposition of saccharides without solvent, but with equimolar amounts of catalyst. The pyridine hydrochloride catalyst is, however, unsuitable for an industrial use of the process. Furthermore, addition of water is followed by a laborious extraction (20 h) with ethyl acetate.

This is also expressed in the publication by D. W. Brown et al., J. Chem. Tech. Biotechnol. 32, 920 (1982), where it is stated analogously that the more recent methods of preparing 5-hydroxymethylfurfural have the disadvantage that the product is present in the aqueous phase or in a polar solvent, from which the isolation is difficult.

EP-A 0 230 250 describes a process for preparing 5-hydroxymethylfurfural, in which saccharides are decomposed with an acidic catalyst in aqueous solution, optionally with addition of organic solvents, above 100° C. After removing any solvents present, the reaction mixture is chromatographed by means of ion exchange columns with exclusive use of water as the solvent, a mixed fraction obtainable when a relatively large amount is applied is rechromatographed, and the 5-hydroxymethylfurfural is crystallized out of the corresponding fractions. Although the process described purportedly leads to 5-hydroxymethylfurfural in high purity, the multiple chromatography and crystallization is too complicated and expensive on the industrial scale.

Further processes for preparing 5-hydroxymethylfurfural are disclosed, for example, in Bull. Soc. Chem. France 1987, 5, 855; J. Chem. Tech. Biotechnol. 1992, 55, 139; FR-A-2 669 635; FR-A-2 664 273; U.S. Pat. Nos. 3,483,228; 2,917,520; 3,071,599; 3,066,150 and 2,750,394.

SUMMARY OF THE INVENTION

As is evident from the above examples, the greatest problem in the preparation of 5-hydroxymethylfurfural, particularly on the industrial scale, is to remove this product from starting materials, by-products and solvents. It is therefore an object of the present invention to provide a process for preparing 5-hydroxymethylfurfural, in which the product is obtained in high purity. At the same time, the preparation process should be performable with acceptable yields of 5-hydroxymethylfurfural and in an economically viable manner. Especially in the later use of 5-hydroxymethylfurfural as a medicament, it is crucial that no highly toxic substances are used in the preparation.

The above and other objects is achieved by a process for preparing 5-hydroxymethylfurfural via a 5-acyloxymethylfurfural as an intermediate. The first embodiment of the present invention includes a process for preparing a 5-acyloxymethylfurfural, comprising:

(a) reacting a saccharide having 6 carbon atoms in the monosaccharide unit with
  (i) an acid which is not an acidic ion exchanger in the presence of a metal cation selected from the group consisting of alkali metal ions, alkaline earth metal ions, aluminum ions and mixtures thereof, or
  (ii) an acidic ion exchanger in the H form in the presence of a polar aprotic solvent, and removing the acidic ion exchanger, thereby obtaining a mixture;

(b) adding an anhydride and/or chloride of a carboxylic acid R—(—COOH)$_x$ wherein R and x are each as defined in formula (II) to the mixture from step (a) and allowing them to react in order to form a 5-acyloxymethylfurfural of formula (II); and (c) recovering the 5-acyloxymethylfurfural of the formula (II)

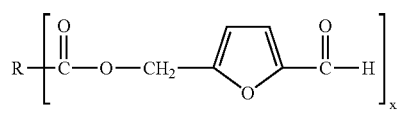

wherein
x=1 or 2,
R is an alkyl, alkenyl, aryl or heteroaryl radical when x=1,
R is an alkylene, alkenylene, arylene or heteroarylene radical when x=2.

In another embodiment, the present invention provides a process for preparing 5-hydroxymethylfurfural of formula (I)

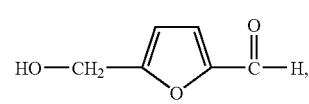

comprising:

preparing a 5-acyloxymethylfurfural a above; and
(d) dissolving the 5-acyloxymethylfurfural in an alcohol, thereby obtaining a solution;
(e) adding a base selected from the group consisting of (i) alkali metal carbonates and hydrogencarbonates, alkaline earth metal carbonates and hydroxides, basic salts of alkaline earth metals, aluminum carbonate, aluminum hydroxide, aluminum oxide hydroxide, and basic salts of aluminum, mixtures of the above and (ii) basic ion exchangers in the OH form, to the solution from step (d) and allowing them to react in order to form 5-hydroxymethylfurfural, and
(f) recovering the 5-hydroxymethylfurfural.

DETAILED DESCRIPTION OF THE INVENTION

The present invention therefore provides both a process for preparing 5-acyloxymethylfurfural of the formula (II)

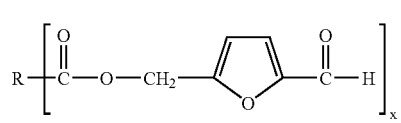

in which
x=1 or 2,
R is an alkyl, alkenyl, aryl or heteroaryl radical when x=1,
R is an alkylene, alkenylene, arylene or heteroarylene radical when x=2,
from a saccharide having 6 carbon atoms in the monosaccharide unit, comprising the steps of:
(a) reacting the saccharide with
(i) an acid which is not an acidic ion exchanger in the presence of a metal cation selected from alkali metal ions, alkaline earth metal ions, aluminium ions and mixtures thereof, or
(ii) an acidic ion exchanger in the H form in the presence of a polar aprotic solvent, and removing the acidic ion exchanger, if used,
(b) adding an anhydride and/or chloride of a carboxylic acid R—(—COOH)$_x$ in which R and x are each as defined above to the mixture from step (a) and allowing them to react in order to form a 5-acyloxymethylfurfural, and
(c) recovering the 5-acyloxymethylfurfural,
and the further processing of the 5-acyloxymethylfurfural to 5-hydroxymethylfurfural

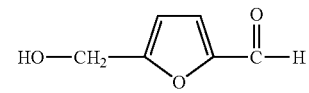

comprising the further steps of:
(d) dissolving the 5-acyloxymethylfurfural in an alcohol,
(e) adding a base selected from (i) alkali metal carbonates and hydrogencarbonates, alkaline earth metal carbonates and hydroxides, basic salts of the alkaline earth metals, aluminium carbonate, aluminium hydroxide, aluminium oxide hydroxide, and basic salts of aluminium, mixtures of the above and (ii) basic ion exchangers in the OH form, to the solution from step (d) and allowing them to react in order to form 5-hydroxymethylfurfural, and (f) recovering the 5-hydroxymethylfurfural.

The starting material for preparing 5-acyloxymethylfurfural or 5-hydroxymethylfurfural is a saccharide having 6 carbon atoms in the monosaccharide unit. In principle, the term "saccharide" also includes mixtures of different saccharides. The starting materials used may also optionally be mixtures which, as well as the saccharide, also comprise other substances, provided that they do not disrupt the process and the saccharide is present in sufficient amount. The term "saccharide" means monosaccharides, oligosaccharides and polysaccharides Monosaccharides and oligosaccharides are also summarized as "sugars". The monosaccharide unit having 6 carbon atoms is also referred to as "hexose", and the term "hexose" herein shall encompass both the aldohexoses and the ketohexoses. Examples of monosaccharides suitable as starting materials are fructose, glucose, mannose, allose, altrose, gulose, idose, galactose and talose. Examples of oligosaccharides suitable as starting materials are the disaccharides, for instance sucrose, isomaltose, gentiobiose, melibiose, trehalose, mannopyranosylmannopyranose, maltose, lactose, trehalose and cellobiose, and trisaccharides, for instance raffinose. Examples of polysaccharides suitable as starting materials are the fructans (polysaccharides having 10 to 40 fructose units), for instance inulin, and also starch and cellulose. The saccharide used is preferably a sugar or a saccharide mixture which comprises sugar. The saccharide used is more preferably selected from D-fructose in free form, a saccharide which comprises D-fructose in bound form (e.g. sucrose, inulin), and a saccharide mixture which comprises D-fructose in free form and/or a saccharide which comprises D-fructose in bound form.

The inventive preparation of 5-hydroxymethylfurfural proceeds via a 5-acyloxymethylfurfural of the formula (II) as an intermediate. In formula (II), R is a monovalent or divalent group. When x=1, R is an alkyl group, preferably $C_1$- to $C_{20}$-alkyl; an alkenyl group, preferably ethenyl; an aryl group, preferably phenyl, or a heteroaryl group, for instance pyridyl, pyrimidyl, pyrazinyl, pyrrolyl, furanyl or thiophenyl. When x=2, R is an alkylene group, preferably $C_1$- to $C_{20}$-alkylene; an alkenylene group, preferably ethenylene; an arylene group, preferably phenylene, or a heteroarylene group, for instance pyridylene, pyrimidylene, pyrazinylene, pyrrolylene, furanylene or thiophenylene. More preferably, R is methyl, i.e. 5-acetoxymethylfurfural is prepared as the intermediate.

In step (a) of the process according to the invention, the saccharide is reacted either (i) with an acid in the presence of a metal cation or (ii) with an acidic ion exchanger in the H form in the presence of a polar aprotic solvent. Among other reactions, the saccharide is dehydrated to 5-hydroxymethylfurfural.

In variant (i), the acid may be any acid which dissolves both the saccharide and the salt which provides the metal cation. Particularly suitable acids are oxalic acid, acetic acid and hydrochloric acid and combinations thereof, preference being given to oxalic acid, and oxalic acid in combination with acetic acid. Aside from the acid, preferably no further solvent is added in step (a)(i), i.e. the acid is preferably used in substantially anhydrous form, though low water contents which might result from the industrial preparation of the acid do not disrupt the reaction. In variant (i), in particular, preference is given to dispensing with the presence of solvents which can be removed later only with difficulty, for instance dimethyl sulphoxide. When acetic acid is used, partial acetylation proceeds as early as in step (a), and 5-acetoxymethylfurfural is formed.

The metal cation in step (a)(i) is selected from alkali metal ions, alkaline earth metal ions, aluminium ions and mixtures thereof. Preference is given to $Mg^{2+}$, $Ca^{2+}$, $Na^+$ and $Al^{3+}$ ions, particular preference to $Mg^{2+}$. The metal cation is advantageously added in the form of a solid salt; very suitable salts are the chlorides, e.g. $MgCl_2$, but also the bromides, e.g. $MgBr_2$, and the fluorides, e.g. $MgF_2$.

Without wishing to be bound to this theory, it is assumed that the cation, e.g. $Mg^{2+}$, stabilizes the furanose form of the hexose, which is believed to play an important role in the formation of the furan compound, in a "sugar-cation complex" and hence catalyses the dehydration.

In a preferred embodiment, the saccharide and the salt containing the metal cation are initially charged and optionally heated, and then the acid is added. In principle, however, any other sequence of combination is also possible.

Typically, the saccharide and the metal cation are used in a molar ratio of 0.5:1 to 2:1, based on the monosaccharide unit, preferably of 1:1 to 1.5:1, particular preference being given to the use of saccharide and metal cation in about equimolar amounts. The saccharide and the metal cation are used in a molar ratio which includes all values and subvalues therebetween, especially including 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1. Since the acid in variant (i) of step (a) also simultaneously serves as the solvent, it is typically used in a large excess, for example in a 2- to 20-fold molar excess based on the monosaccharide unit.

In step (a), variant (ii), the saccharide is reacted with an acidic ion exchanger in the H form in the presence of a polar aprotic solvent, and the ion exchanger is removed again before step (b) is carried out, for example by filtration. The acidic ion exchanger is a cationic organic or inorganic, typically organic, ion exchanger. An organic ion exchanger is a solid polyelectrolyte, usually in particle form, with a three-dimensional, water-insoluble, high molecular weight polymer skeleton (matrix), into which numerous charged "anchor groups" are incorporated. Its loosely bound counterions can be exchanged for other ions with the same kind of charge. The matrix resins used are predominantly styrene copolymers, preferably divinylbenzene-crosslinked polystyrene, and acrylic polymers, for instance the acrylate, methacrylate and acrylonitrile copolymers which are each crosslinked with divinylbenzene. In the case of an acidic ion exchanger in the H form, the anchor groups are acidic groups in their protonated form (acid form), i.e. the exchangeable counterions are $H^+$. In step (a)(i) of the present invention, preference is given to using a strongly acidic cation exchanger in the H form, which bears sulphonic acid groups in their protonated form as anchor groups. It is also possible to use weakly acidic cation exchangers which bear carboxylic acid groups in their protonated form; however, the reaction time will be prolonged in this case. Particular preference is given to a styrene-divinylbenzene copolymer resin with protonated sulphonic acid groups as anchor groups.

Typically, the acidic ion exchanger is used in an amount which corresponds to a large molar excess of the acidic anchor groups based on monosaccharide unit of the saccharide used, preferably a 2- to 20-fold, with preference 10- to 20-fold, molar excess. The molar excess of the acidic anchor groups, based on monosaccharide unit of the saccharide used, includes all values and subvalues therebetween, especially including a 4, 6, 8, 10, 12, 14, 16 and 18-fold molar excess.

The number of the acidic anchor groups and hence the required amount of the ion exchanger is calculated from the exchange capacity, which is typically reported in equivalents/l or equivalents/kg.

Examples of polar aprotic solvents suitable in step (a)(ii) include dimethyl sulphoxide (DMSO), N-methylpyrrolidone (NMP), dimethylformamide, N,N-dimethylacetamide, acetonitrile and mixtures thereof. Preference is given to DMSO and NMP, particular preference to NMP.

Typically, the saccharide and the polar aprotic solvent are used in a molar ratio of 1:2 to 1:20, preferably of 1:2 to 1:10. The saccharide and the polar aprotic solvent are used in a molar ratio which includes all values and subvalues therebetween, especially including 1:2, 1:4, 1:6, 1:8, 1:10, 1:12, 1:14, 1:16 and 1:18. In a preferred embodiment, step (a) is performed at a temperature of 80 to 140° C., more preferably of 80 to 110° C., at a reaction time of 4 to 7 h, more preferably of 4 to 6 h. In the case of correspondingly longer reaction times, it is also possible to employ lower temperatures. The upper limit in the temperature results from the boiling point of the reaction mixture. The temperature of step (a) includes all values and subvalues therebetween, especially including 85, 90, 85, 100, 105, 110, 115, 120, 125, 130 and 135° C. The reaction time includes all values and subvalues therebetween, especially including 4.5, 5, 5.5, 6 and 6.5 hours.

In step (b), an anhydride and/or chloride of a carboxylic acid R—(—COOH)$_x$ in which R and x are each as defined above is added to the mixture from step (a), and the acetylation proceeds to give a 5-acyloxymethylfurfural. As already mentioned above, R is preferably methyl, i.e. acetic anhydride and/or acetyl chloride is preferably added in step (b), particular preference being given to acetic anhydride, and 5-acetoxymethylfurfural is formed. When acidification has been effected in step (a) with acetic acid and partial acetylation has thus already proceeded in this first step, the acetylation is then completed in step (b) by the addition of acetic anhydride and/or acetyl chloride.

Further illustrative anhydrides and chlorides which can be used in step (b) of the present invention are immediately evident from the aforementioned examples of the R group. It is obvious that, when a 5-acyloxymethylfurfural where x=2 is to be obtained, the corresponding dicarboxylic acids have to be used. Many dicarboxylic acids form cyclic anhydrides owing to their molecular structure. Very suitable anhydrides are, for instance, the inexpensive anhydrides of maleic acid, fumaric acid, pyridyl-2,3-dicarboxylic acid and pyrazine-2,3-dicarboxylic acid.

In a preferred embodiment of the present invention, step (b) is performed in the presence of a basic catalyst, for example 4-(N,N-dimethylamino)pyridine. The basic catalyst is typically added in catalytic amounts, for instance in a molar ratio of catalyst to monosaccharide unit of 1:10 to 1:100. The a molar ratio of catalyst to monosaccharide unit includes all values and subvalues therebetween, especially including 1:20, 1:30, 1:40, 1:50, 1:60, 1:70, 1:80 and 1:90.

Owing to the water of reaction which forms, in variant (i) of the present process, the anhydride and/or chloride of the carboxylic acid R—(—COOH)$_x$ is typically added in a large molar excess. Preference is given to using an equivalents ratio of monosaccharide unit of the saccharide used at the start to anhydride and/or chloride of the carboxylic acid R—(—COOH)$_x$ of at least 1:4, more preferably of 1:4 to 1:12. The equivalents ratio of monosaccharide unit of the saccharide used at the start to anhydride and/or chloride of the carboxylic acid R—(—COOH)$_x$ includes all values and subvalues therebetween, especially including 1:5, 1:6, 1:7, 1:8, 1:9, 1:10 and 1:11.

In variant (ii) of the present process, the monosaccharide unit and the anhydride and/or chloride of the carboxylic acid R—(—COOH)$_x$ are used typically in an equivalents ratio of 1:0.7 to 1:3, preferably of 1:0.8 to 1:1.2, particular preference being given to the use of the monosaccharide unit and of the anhydride and/or chloride of the carboxylic acid R—(—COOH)$_x$ in about equivalent amounts (i.e. equimolar amounts for x=1). The equivalents ratio of monosaccharide unit of the saccharide to anhydride and/or chloride of the carboxylic acid R—(—COOH)$_x$ includes all values and subvalues therebetween, especially including 1:0.8, 1:0.9, 1:1, 1:1.1 and 1:1.2. Without wishing to be bound to this theory, it is suspected that the water of reaction formed is bound to the ion exchanger.

Preference is given to effecting step (b) with stirring.

Typically, step (b) is performed at a temperature of 0 to 40° C. at a reaction time of 0.5 to 3 h. The temperature includes all values and subvalues therebetween, especially including 5, 10, 15, 20, 25, 30 and 35° C. The reaction time includes all values and subvalues therebetween, especially including 1, 1.5, 2 and 2.5 hours. For correspondingly longer reaction times, lower temperatures can also be employed. Since the acylation reaction is exothermic, it may be necessary to cool. The upper limit in the temperature arises from the boiling point of the reaction mixture.

In order to shift the equilibrium of the acylation reaction in step (b) to the right, it is advantageous to remove the carboxylic acid R—(—COOH)$_x$ formed from the mixture. This can be done by customary measures, for example by distillative removal, optionally with addition of an aprotic water-immiscible organic solvent, for instance toluene, xylene, tert-butyl methyl ether (MtBE), methyl isobutyl ketone (MIBK), more preferably MtBE. In this case, 5-acyloxymethylfurfural is obtained dissolved in the organic solvent. When step (a) of the process according to the invention has been performed by variant (ii), i.e. in the presence of a polar aprotic solvent, it is then preferably also distilled off for the most part in step (b). In that case too, the distillation can be effected with addition of the abovementioned aprotic water-immiscible organic solvents.

In the subsequent step (c), the 5-acyloxymethylfurfural is recovered, i.e. freed from the undesired by-products, unconverted starting materials and any solvent. The 5-acyloxymethylfurfural is purified by methods customary in industry, for example by extraction, filtration, distillation and combinations thereof. For the extraction, water and an aprotic water-immiscible organic solvent are added as described above, if the latter has not already been added in step (b). Also advantageous is the addition of activated carbon in order to bind thereon polymeric by-products which are soluble neither in water nor in the organic solvent. The activated carbon can then be filtered off together with the solid by-products, if appropriate with addition of a filtering aid, for instance Celite®. The aqueous phase is then removed from the organic phase in which the desired 5-acyloxymethylfurfural product is present, the organic solvent is distilled off and the remaining 5-acyloxymethylfurfural is distilled for fine purification, preferably under reduced pressure. The manner of workup of the 5-acyloxymethylfurfural intermediate is, however, not essential for the present invention, and any other suitable process for recovering the 5-acyloxymethylfurfural is also possible.

Typically, the yields of 5-acyloxymethylfurfural, based on saccharide, are 20 to 80%, preferably 30 to 80%, more preferably 40 to 80% and most preferably 42 to 80%. The yield of 5-acyloxymethylfurfural, based on saccharide includes all values and subvalues therebetween, especially including 25, 30, 35, 40, 45, 50, 55, 60, 65, 70 and 75%.

If the 5-acyloxymethylfurfural is to be processed further to 5-hydroxymethylfurfural, it is dissolved in step (d) in an alcohol, preferably an aliphatic primary or secondary alcohol, for instance methanol, ethanol, propanol, butanol, pentanol, hexanol, isopropanol or isobutanol, or benzyl alcohol, if appropriate while applying heat. Particular preference is given to using methanol as the alcohol, in which, for example, 5-acetoxymethylfurfural dissolves readily even at room temperature (approx. 20-25° C.). Typically, the 5-acyloxymethylfurfural is dissolved in the alcohol in a molar ratio of 1:5 to 1:10. The 5-acyloxymethylfurfural is dissolved in the alcohol in a molar ratio which includes all values and subvalues therebetween, especially including 1:6, 1:7, 1:8, and 1:9.

Then, in step (e), a base selected from (i) alkali metal carbonates and hydrogencarbonates, alkaline earth metal carbonates and hydroxides, basic salts of the alkaline earth metals, aluminium carbonate, aluminium hydroxide, aluminium oxide hydroxide and basic salts of aluminium, mixtures of the above and (ii) basic ion exchangers in the OH form is added, and hydrolysis of the acyl group (ester group) forms the desired 5-hydroxymethylfurfural product. Preferred bases are a basic ion exchanger in the OH form, potassium carbonate, sodium carbonate and calcium carbonate, particular preference being given to a basic ion exchanger in the OH form and potassium carbonate.

The basic ion exchanger is an anionic organic or inorganic, typically organic, ion exchanger. Organic ion exchangers and their matrix polymers have already been described above in general terms. In a basic ion exchanger in the OH form, the anchor groups are positively charged groups and the exchangeable counterions are $OH^-$. In step (e) of the present invention, preference is given to using a strongly basic anion exchanger which bears quaternary ammonium groups, especially benzyltrimethylammonium groups (known as "type 1") or benzyldimethylethanolammonium groups (known as "type 2") as anchor groups, and contains hydroxide ions as counterions. It is also possible to use weakly basic anion exchangers with tertiary amino groups. Particular preference is given to a styrene-divinylbenzene copolymer resin with benzyltrimethylammonium groups as anchor groups in its OH form, e.g. AMBERLYST® A26 OH, obtainable from Rohm and Haas Company, Philadelphia, U.S.A.

In both variants of step (e), the 5-acyloxymethylfurfural and the base are used typically in an equivalents ratio of 1:0.9 to 1:3, preferably of 1:1 to 1:2, more preferably of 1:1 to 1:1.5, preference being given to about equivalent amounts of the two reactants. When a basic ion exchanger is used, the amount thereof required is calculated, taking account of the aforementioned equivalents ratios, from the exchange capacity, which is typically reported in equivalents/l or equivalents/kg.

The hydrolysis in step (e) is effected preferably at a relatively low temperature (approx. 20-35° C.) for a reaction time of 1 to 3 h. According to the type of acyl radical of the 5-acyloxymethylfurfural, however, it is also possible to employ higher temperatures. The temperature includes all values and subvalues therebetween, especially including 22, 24, 26 and 28° C. The reaction time includes all values and subvalues therebetween, especially including 1.5, 2 and 2.5 hours.

In the subsequent step (f), the 5-hydroxymethylfurfural is recovered, i.e. freed from the undesired by-products, unconverted starting materials, solid ion exchanger if used, and solvent. The 5-hydroxymethylfurfural is purified by methods customary in industry, for example filtration, distillation and/or crystallization. Preference is given to first filtering off the solid by-products and, if used, the ion exchanger, and then distilling the filtrate in order to recover the 5-hydroxymethylfurfural in pure form. Since 5-hydroxymethylfurfural is thermally sensitive and tends to form polymers and ethers among other substances, it is advisable to carry out a molecular distillation or short-path distillation under reduced pressure, for example with the aid of a short-path evaporator, falling-film evaporator or thin-film evaporator. Short-path distillation is a distillation technique that involves the distillate traveling a short distance, often only a few centimeters. However, the traveling distance is not limited to a distance of a few centimeters. A classic example would be a distillation involving the distillate traveling from one glass bulb to another, without the need for a condenser separating the two chambers. This technique is often used for compounds which are unstable at high temperatures. Advantages are that the temperature of the boiling liquid does not have to be much higher than the boiling point of the distilling substance, and the gases only have to travel a short distance while in the gas-phase before they can be cooled again to a lower temperature.

In another preferred embodiment, the 5-hydroxymethylfurfural, after filtration, is recovered by crystallization from a suitable solvent, for instance diethyl ether, diisopropyl ether, MtBE or tert-butyl ethyl ether (EtBE), preferably MtBE, at a suitable temperature.

Typically, the yield of 5-hydroxymethylfurfural, based on saccharide, is 10 to 70%, preferably 20 to 70%, more preferably 25 to 70% and most preferably 30 to 70%. The yield of 5-hydroxymethylfurfural, based on saccharide includes all values and subvalues therebetween, especially including 25, 30, 35, 40, 45, 50, 55, 60 and 65%.

Typically, in the process according to the invention, 5-hydroxymethylfurfural is obtained in a purity of at least 90%, preferably at least 95%, more preferably at least 98% and most preferably at least 99%. The purity includes all values and subvalues therebetween, especially including 91, 92, 93, 94, 95, 96, 97, 98, 99, 99.1, 99.2, 99.3, 99.4, 99.5, 99.6, 99.7, 99.7, 99.8, 99.9 and 99.95%. The purity is thus above the purity achievable with comparable chromatography-free processes. The high achievable purity makes the 5-hydroxymethylfurfural prepared in accordance with the invention suitable for cosmetic or pharmaceutical purposes.

In the present invention, for the first time, a process is provided for preparing 5-hydroxymethylfurfural, which enables industrial scale production of 5-hydroxymethylfurfural in high purity.

Having generally described this invention, a further understanding can be obtained by reference to certain specific examples which are provided herein for purposes of illustration only, and are not intended to be limiting unless otherwise specified.

EXAMPLES

Example 1A

Preparation of 5-acetoxymethylfurfural Using $MgCl_2$ 107 g (0.6 mol) of D-fructose and 122 g (0.6 mol) of $MgCl_2.6H_2O$ were introduced into a 2 l three-neck flask with stirring and heated to 75° C. for 30 min. The reaction mixture was admixed with 420 ml of anhydrous acetic acid (glacial acetic acid) and heated to 90-95° C. for 4 h. Thereafter, approx. 80% of the acetic acid was distilled off, the mixture was cooled to room temperature and 5 g (0.04 mol) of 4-(N, N-dimethylamino)pyridine were added. With stirring, 616 ml (6.5 mol) of acetic anhydride were added drop wise to the reaction mixture at 30-40° C., and the 600-700 ml of acetic acid were distilled off. At approx. 80° C., the reaction mixture was admixed slowly with 500 ml of water, 500 ml of MIBK and 50 g of activated carbon. After filtration through a pressure filter, the organic phase and aqueous phase were separated. The organic phase was freed of the solvent on a rotary evaporator and the residue was distilled under reduced pressure at 117-125° C./7 mbar.

Yield: 45.9 g (0.27 mol, 45%) of 5-acetoxymethylfurfural.

Example 1B

Hydrolysis of 5-acetoxymethylfurfural Using Potassium Carbonate 179.1 g (1.07 mol) of the 5-acetoxymethylfurfural prepared in Example 1A were dissolved in 1.1 l of methanol and admixed at 20-25° C. with 140 g (1.01 mol) of potassium carbonate with stirring. After 1 h, the reaction mixture was admixed with 10 g of activated carbon and stirred for 20 min, and the solid constituents were filtered off and washed with 100 ml of MeOH. The clear methanolic solution was concentrated under reduced pressure on a rotary evaporator. The residue was admixed with 300 ml of MtBE. The precipitated salts were filtered off and washed with 20 ml of MtBE. The solution was concentrated on a rotary evaporator and the residue was distilled in a short-path evaporator at 90° C./0.03 mbar. Yield: 85.2 g (0.68 mol, 63% based on 5-acetoxymethylfurfural, 29% based on D-fructose). Alternatively, the residue can also be admixed with MtBE, and the product crystallized at 0° C. (yield: 98.4 g) (0.78 mol, 73% based on 5-acetoxymethylfurfural, 33% based on D-fructose)).

Example 2A

Preparation of 5-acetoxymethylfurfural Using an Acidic Ion Exchanger 39.4 kg (219 mol) of D-fructose and 5.9 kg of dried acidic Dowex® 50WX8-200 ion exchanger (styrene-divinylbenzene copolymer resin with $SO_3H$ groups, obtainable from The Dow Chemical Company, Midland, U.S.A.) in the H form were introduced with stirring into 90 l of NMP and heated to 110° C. for 6 h. After cooling, the reaction mixture was filtered and washed with 8 l of NMP. The filtrate was admixed with stirring with 390 g (3.2 mol) of 4-(N,N-dimethylamino)pyridine and 20.5 l (217 mol) of acetic anhydride at 20-25° C. within 1 h. After continuing the reaction for 1 h, the brown reaction mixture was freed of the solvent at 90-100° C. under reduced pressure (of 50-10 mbar). After cooling, the residue was admixed with 160 l of MtBE, 60 l of water and 4 kg of activated carbon. The suspension was filtered though Celite®. After the phase separation, the solvent of the filtrate was distilled off at 50° C. under reduced pressure (20 mbar) and the residue was fractionally distilled under reduced pressure at 106-110° C./5 mbar.

Yield: 15.5 kg (92 mol, 42%) of 5-acetoxymethylfurfural

Example 2B

Hydrolysis of 5-acetoxymethylfurfural Using a Basic Ion Exchanger 10.9 kg (65 mol) of 5-acetoxymethylfurfural were dissolved in 60 l of methanol and admixed with stirring with 1.1 kg of dried strongly basic Amberlyst® A26 OH ion exchanger (styrene-divinylbenzene copolymer resin with quaternary ammonium groups (type 1) in OH form, obtainable from Rohm and Haas Company, Philadelphia, U.S.A.) at 25-30° C. After 1 h, the reaction mixture was admixed with 1 kg of activated carbon, stirred for 60 min, filtered through Celite® and washed with 10 l of methanol. The clear methanolic solution was concentrated at not more than 40° C. under reduced pressure. The residue was admixed with 8 l of MtBE and cooled slowly to 5° C. The precipitated product was filtered off with suction, washed with 1.5 l of ice-cold MtBE and dried at 20° C. under reduced pressure.

Yield: 7.01 kg (56 mol, 86% based on 5-acetoxymethylfurfural, 36% based on D-fructose) of 5-hydroxymethylfurfural. Alternatively, the residue can be distilled in a short-path evaporator at 90° C./0.03 mbar (yield: 5.42 kg (43 mol, 67% based on 5-acetoxymethylfurfural, 28% based on D-fructose)).

The purity of the 5-hydroxymethylfurfural prepared was >99% in all examples, as determined with the aid of HPLC and NMR.

German patent application 10 2007 007 629.2 filed Feb. 16, 2008, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for preparing a 5-acyloxymethylfurfural, comprising:
   (a) reacting at ambient pressure a saccharide comprising a monosaccharide unit having 6 carbon atoms with
      (i) an acid which is not an acidic ion exchanger in the presence of a metal cation selected from the group consisting of alkali metal ions, alkaline earth metal ions, aluminum ions and mixtures thereof,
   thereby obtaining a mixture;
   (b) adding an anhydride and/or chloride of a carboxylic acid R—(—COOH)$_x$ wherein R and x are each as defined in formula (II) to the mixture from (a) and allowing them to react to form a 5-acyloxymethylfurfural of formula (II); and
   (c) recovering the 5-acyloxymethylfurfural of the formula (II)

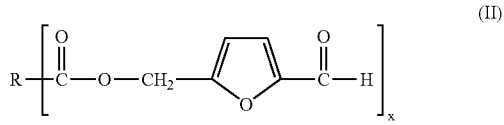

wherein
x =1 or 2,
R is an alkyl, alkenyl, aryl or heteroaryl radical when x =1,
R is an alkylene, alkenylene, arylene or heteroarylene radical when x =2.

2. The process according to claim 1, wherein R is methyl.

3. The process according to claim 1, wherein acetic anhydride is added in (b).

4. The process according to claim 1, wherein the acid in (a)(i) is at least one selected from the group consisting of oxalic acid, acetic acid, and hydrochloric acid.

5. The process according to claim 1, wherein the metal cation in (a)(i) is $Mg^{2+}$.

6. The process according to claim 1, wherein the saccharide reacted in (a) is a sugar or a saccharide mixture which comprises sugars.

7. The process according to claim 1, wherein the saccharide used in (a) is selected from the group consisting of D-fructose in free form, a saccharide which contains D-fructose in bound form, and a saccharide mixture which contains D-fructose in free form, a saccharide which contains D-fructose in bound form and mixtures thereof.

8. The process according to claim 1, wherein reaction (b) is conducted in the presence of a basic catalyst.

9. The process according to claim 8, wherein the basic catalyst is 4-(N,N-dimethylamino)pyridine.

10. A process for preparing 5-hydroxymethylfurfural of formula (I)

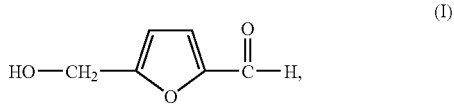

comprising:

preparing a 5-acyloxymethylfurfural according to claim 1; and (d) dissolving the 5-acyloxymethylfurfural in an alcohol, thereby obtaining a solution;

(e) adding a base selected from the group consisting of (i) alkali metal carbonates and hydrogencarbonates, alkaline earth metal carbonates and hydroxides, basic salts of alkaline earth metals, aluminum carbonate, aluminum hydroxide, aluminum oxide hydroxide, and basic salts of aluminum, mixtures of the above and (ii) basic ion exchangers in the OH form, to the solution from step (d) and allowing them to react in order to form 5-hydroxymethylfurfural, and (f) recovering the 5-hydroxymethylfurfural.

11. The process according to claim 10, wherein the alcohol for dissolving the 5-hydroxymethylfurfural in step (d) is methanol.

12. The process according to claim 10, wherein the base in step (e) is potassium carbonate.

13. The process according to claim 10, wherein the recovery of the 5-hydroxymethylfurfural in step (f) comprises a short-path distillation of the 5-hydroxymethylfurfural.

14. The process according to claim 10, wherein the recovery of the 5-hydroxymethylfwfural in step (f) comprises crystallization of the 5-hydroxymethylfurfural from a suitable solvent.

* * * * *